(12) United States Patent
Kimura et al.

(10) Patent No.: US 6,627,642 B1
(45) Date of Patent: Sep. 30, 2003

(54) QUINOLINONE DERIVATIVE PREPARATIONS AND PROCESS FOR PRODUCING THE SAME

(75) Inventors: Nobuyuki Kimura, Sakura (JP); Hiroyuki Fukui, Sakura (JP); Hidetsugu Takagaki, Sakura (JP); Nahoko Muratake, Urawa (JP)

(73) Assignee: Dainippon Ink and Chemicals, Inc., Tokyo (JP)

( * ) Notice: Subject to any disclaimer, the term of this patent is extended or adjusted under 35 U.S.C. 154(b) by 0 days.

(21) Appl. No.: 09/830,584

(22) PCT Filed: Sep. 10, 1999

(86) PCT No.: PCT/JP99/04920

§ 371 (c)(1),
(2), (4) Date: May 8, 2001

(87) PCT Pub. No.: WO01/19368

PCT Pub. Date: Mar. 22, 2001

(51) Int. Cl.[7] .................................................. A61K 31/47
(52) U.S. Cl. ...................................................... 514/311
(58) Field of Search .......................................... 514/311

(56) References Cited

U.S. PATENT DOCUMENTS 5,179,203 A * 1/1993 Ao et al. ........................ 544/8

FOREIGN PATENT DOCUMENTS

| EP | 0 785 190 A2 | 7/1997 |
| EP | 0927718 A | 7/1999 |
| EP | 0933378 A | 8/1999 |
| JP | 9-255659 | 9/1997 |
| JP | 11-255649 | 9/1999 |

OTHER PUBLICATIONS

Proceedings of the 12th Annual Convention of the Japan Pharmaceutical Society published on Mar. 14, 1997.

* cited by examiner

*Primary Examiner*—Kevin E. Weddington
(74) *Attorney, Agent, or Firm*—Armstrong, Westerman, & Hattori, LLP

(57) ABSTRACT

The problem to be solved by the present invention is to provide a quinolinone derivative formulation, and its production method, having for its active ingredient the β crystal form and/or γ crystal form of the quinolinone derivative represented with chemical formula (I), which is useful as a pharmaceutical, and particularly as an antiallergic, which has superior bioabsorption and stability. The present invention provides a quinolinone derivative, and its production method, having for its active ingredient the β crystal form and/or γ crystal form of the quinolinone derivative represented with chemical formula (I):

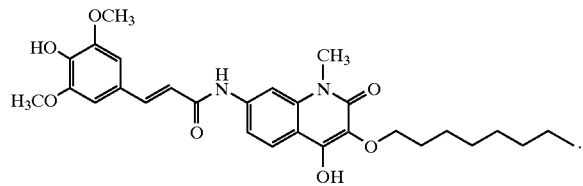

4 Claims, 4 Drawing Sheets

QUINOLINONE DERIVATIVE PREPARATIONS AND PROCESS FOR PRODUCING THE SAME

TECHNICAL FIELD

The present invention relates to a quinolinone derivative formulation having superior stability and bioabsorption, and its production method.

The present specification is based on a Japanese patent application filed in Japan (Japanese Patent Application No. Hei 10-62907), and the described contents of said Japanese patent application are incorporated as a portion of the present specification.

BACKGROUND ART

The inventors of the present invention reported in Japanese Unexamined Patent Application, First Publication No. Hei 9-255659 that a novel quinolinone derivative represented with chemical formula (I) has low toxicity, is effective against both immediate and delayed allergies, and is extremely useful as an antiallergic.

In addition, the inventors of the present invention also reported at the 12$^{th}$ Annual Convention of the Japan Pharmaceutical Society (Ohmiya, 1997) that the quinolinone derivative represented with chemical formula (I) demonstrates crystal polymorphism consisting of four crystal types of the α, β, γ and δ forms, and that each form exhibits different absorption in the body. However, the stability of these four crystal forms along with the preferable forms as pharmaceutical formulations were not clarified.

DISCLOSURE OF THE INVENTION

An object of the present invention is to provide a quinolinone derivative, having for its active ingredient the β-form crystal and/or γ-form crystal of a quinolinone derivative represented with chemical formula (I) that is useful as a pharmaceutical, and particularly as an antiallergic, and having superior bioabsorption and stability, along with its production method.

As a result of eager research to achieve the above object, the inventors of the present invention found that, although each crystal form of the quinolinone derivative represented with chemical formula (I) is converted to an amorphous form resulting in improved bioabsorption as a result of crushing, the β, γ and δ crystal forms demonstrate superior bioabsorption as compared with the α crystal form, and the α, β and γ crystal forms demonstrate superior stability as compared with the δ crystal form. Thus, the inventors found that a pharmaceutical formulation having for its active ingredient the β crystal form and/or γ crystal form demonstrates the most superior bioabsorption and stability. Moreover, the inventors found that a pharmaceutical formulation has even more superior stability by adding antioxidant and/or lubricant to a pharmaceutical formulation having for its active ingredient the β crystal form and/or γ crystal form. Thereby, the inventors are led to completion of the present invention.

Namely, the present invention provides the following:

(1) quinolinone derivative formulation including for its active ingredient a β crystal form and/or a γ crystal form of a quinolinone derivative represented with chemical formula (I):

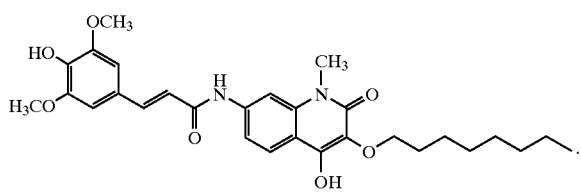

(2) a quinolinone derivative formulation including for its active ingredient a β crystal form and/or a γ crystal form of a quinolinone derivative represented with chemical formula (I):

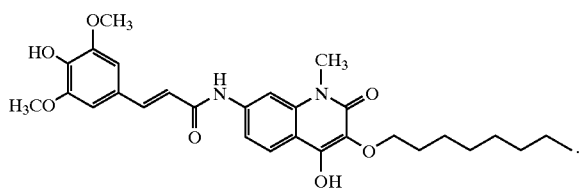

and including an antioxidant and/or a lubricant;

(3) a quinolinone derivative formulation according to (1) or (2), wherein the β crystal form and/or the γ crystal form is obtained by recrystallizing from ethanol;

(4) a quinolinone derivative formulation according to any of (1) through (3), wherein a formulation form of the quinolinone formulation is selected from capsules, coated granules, coated tablets, or sugar-coated tablets, which can block lights;

(5) a production method of a quinolinone derivative formulation comprising: producing a formulation in a formulation form selected from capsules, coated granules, coated tablets, or sugar-coated tablets, which can block lights, by using a β crystal form and/or a γ crystal form of the quinolinone derivative represented with chemical formula (I)

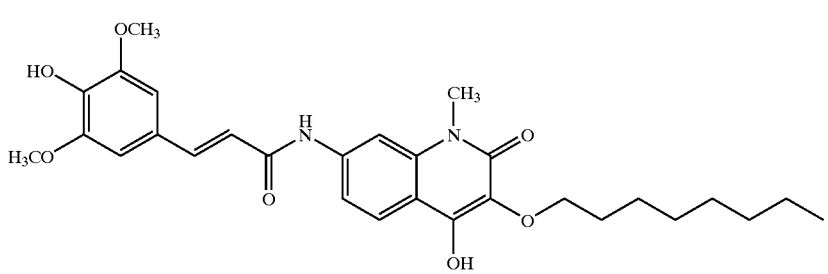

(6) a production method of a quinolinone derivative formulation comprising: producing a formulation in a formulation form selected from capsules, coated granules, coated tablets or sugar-coated tablets, which can block lights, by using a β crystal form and/or a γ crystal form of the quinolinone derivative represented with chemical formula

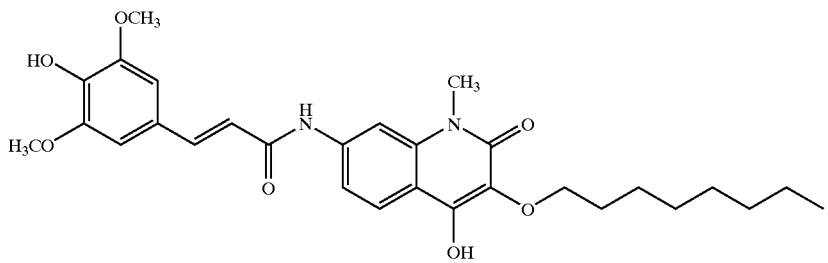

and an antioxidant and/or a lubricant; and (7) a production method of a quinolinone derivative formulation according to (5) or (6), wherein the β crystal form and/or γ crystal form is obtained by recrystallizing from ethanol.

BEST MODE FOR CARRYING OUT THE INVENTION

The quinolinone derivative represented with chemical formula (I) of the present invention was found by the inventors of the present invention to have low toxicity, be effective against both immediate and delayed allergies and be an extremely useful compound for use as an antiallergic, and has been previously described in Japanese Unexamined Patent Application, First Publication No. Hei 9-255659.

However, as a result of further research, it was determined that said quinolinone derivative exists in four types of crystal forms, and that those four types of crystal forms each have different bioabsorption and stability. These four types of crystal forms refer to four types of crystal forms consisting of the α crystal form, δ crystal form, γ crystal form, and δ crystal form of the quinolinone derivative represented with chemical formula (I), and each of these crystal forms are identified by their powder X ray diffraction patterns and differential scanning calorimetry (DSC) curves.

Figure 1:
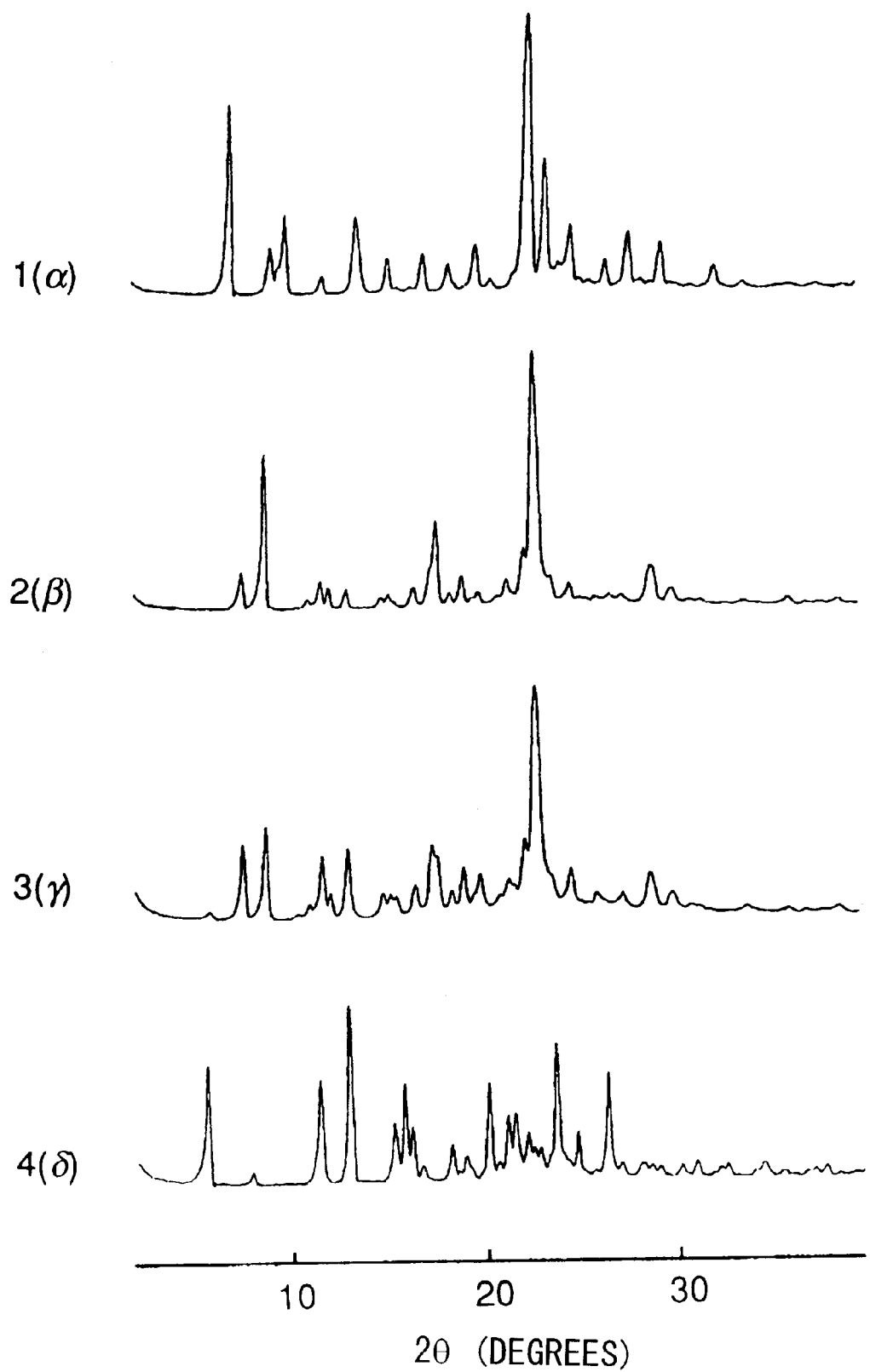
FIG. 1 is a schematic drawing pertaining to powder X-ray diffraction patterns for four types of crystal forms of a quinolinone derivative. 1(α) is the powder X-ray diffraction pattern of the α crystal form, 2(β) is that of the β crystal form, 3(γ) is that of the γ crystal form, and 4(δ) is that of the δ crystal form.

FIG. 1 shows powder X-ray diffraction patterns measured for each crystal of the quinolinone derivative represented with chemical formula (I) under conditions of using a Cu—Kα beam at 40 kV, 30 mA and 2–60°. The horizontal axes in FIG. 1 indicate the angle, 2θ (degrees), while the vertical axes indicate intensity (cps). 1(α) in FIG. 1 indicates the powder X-ray diffraction pattern of the a crystal form, 2(β) that of the β crystal form, 3(γ) that of the γ crystal form, and 4(δ) that of the δ crystal form.

As is clear from FIG. 1, in the case of measuring the powder X-ray diffraction patterns using a Cu—Kα beam at 40 kV, 30 mA and 2–60°, diffraction peaks are exhibited that characterize each crystal form, with the a crystal form exhibiting peaks at 7.14°, 10.1°, 22.8° and 7.14°, the β crystal form at 7.62°, 8.84°, 17.8° and 22.8°, the γ crystal form at 7.68°, 8.88°, 11.8°, 13.2° and 22.9°, and the δ crystal form at 5.74°, 11.6°, 13.2°, 16.0°, 20.4°, 23.9° and 26.6°.

Figure 2:
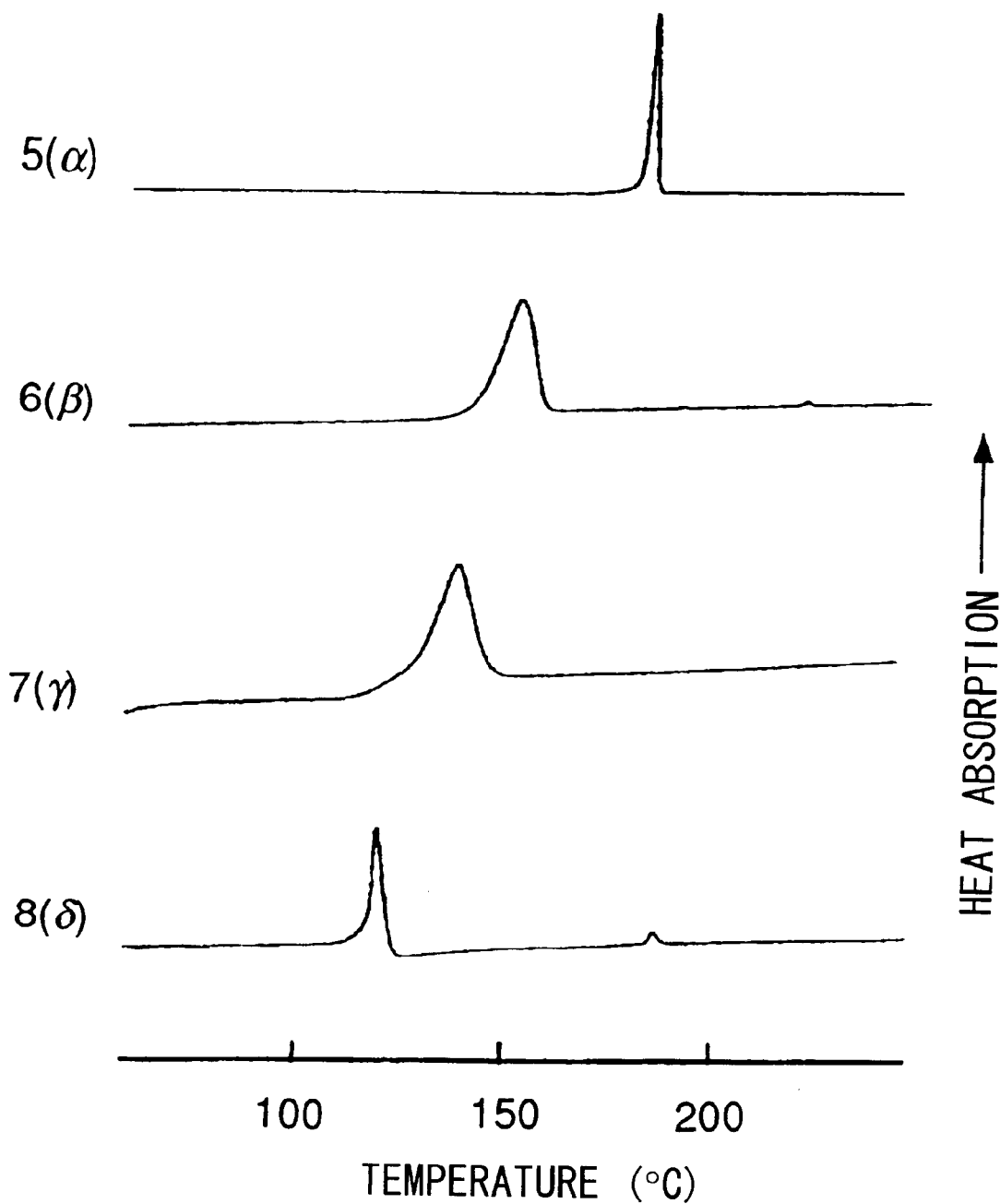
FIG. 2 is a schematic drawing pertaining to DSC curves for four types of crystal forms of a quinolinone derivative. 5(α) is the DSC curve of the α crystal form, 6(β) is that of the β crystal form, 7(γ) is that of the γ crystal form, and 8(δ) is that of the δ crystal form.

In addition, FIG. 2 shows the DSC curves of each crystal form measured at a temperature increase rate of 20° C./min and over a measuring range of 50–250° C. The horizontal axes in FIG. 2 indicate temperature (°C.) while the vertical axes indicate heat absorption (mW). In FIG. 2, 5(α) indicates the DSC curve of the α crystal form, 6(β) that of the β crystal form, 7(γ) that of the γ crystal form, and 8(δ) that of the δ crystal form.

As is clear from FIG. 2, in the case of measuring differential scanning calorimetry (DSC) under conditions of a temperature increase rate of 20° C./min and over a measuring range of 50–250° C., endothermic peaks are exhibited that characterize each crystal form, with the α crystal form exhibiting a peak in the vicinity of 187° C., the β crystal form in the vicinity of 151° C., the γ crystal form in the vicinity of 142° C., and the δ crystal form in the vicinity of 117° C.

In the present invention, crystal that exhibits characteristic diffraction peaks in the vicinity of 7.14°, 10.1°, 22.8° and 7.14° in its powder X-ray diffraction pattern under conditions of using a Cu—Kα beam at 40 kV, 30 mA and 2–60°, and exhibits a characteristic endothermic peak in the vicinity of 187° C. in differential scanning calorimetry (DSC) measurement under conditions of a temperature increase rate of 20° C./min and measuring range of 50–250° C. is referred to as the α crystal form, that which exhibits characteristic diffraction peaks in the vicinity of 7.62°, 8.84°, 17.8° and 22.8° in powder X-ray diffraction under the above conditions and exhibits a characteristic endothermic peak in the vicinity of 151° C. in DSC measurement under the above conditions is referred to as the β crystal form, that which exhibits characteristic diffraction peaks in the vicinity of 7.68°, 8.88°, 11.8°, 13.2° and 22.9° in powder X-ray diffraction under the above conditions and exhibits a characteristic endothermic peak in the vicinity of 142° C. in DSC measurement under the above conditions is referred to as the γ crystal form, and that which exhibits characteristic diffraction peaks in the vicinity of 5.74°, 11.6°, 13.2°, 16.0°, 20.4°, 23.9° and 26.6° in powder X-ray diffraction under the above conditions and exhibits a characteristic endothermic peak in the vicinity of 117° C. in DSC measurement under the above conditions is referred to as the δ crystal form.

However, the diffraction peaks obtained by powder X-ray diffraction measurement of these crystals as well as the endothermic peaks of differential scanning calorimetry (DSC) tends to fluctuate slightly as a result being affected by the degree of crystallinity of these crystals. Consequently, in the present invention, the locations of diffraction peaks and endothermic peaks of these crystals are described using the expression, "in the vicinity".

In addition, the degree of crystallinity is affected by mechanically crushing the crystals. As a result, it must be noted that the diffraction peaks of powder X-ray diffraction measurement and the endothermic peaks of differential scanning calorimetry (DSC) characteristic of each crystal are also subjected to the effect of mechanical crushing.

Figure 3:
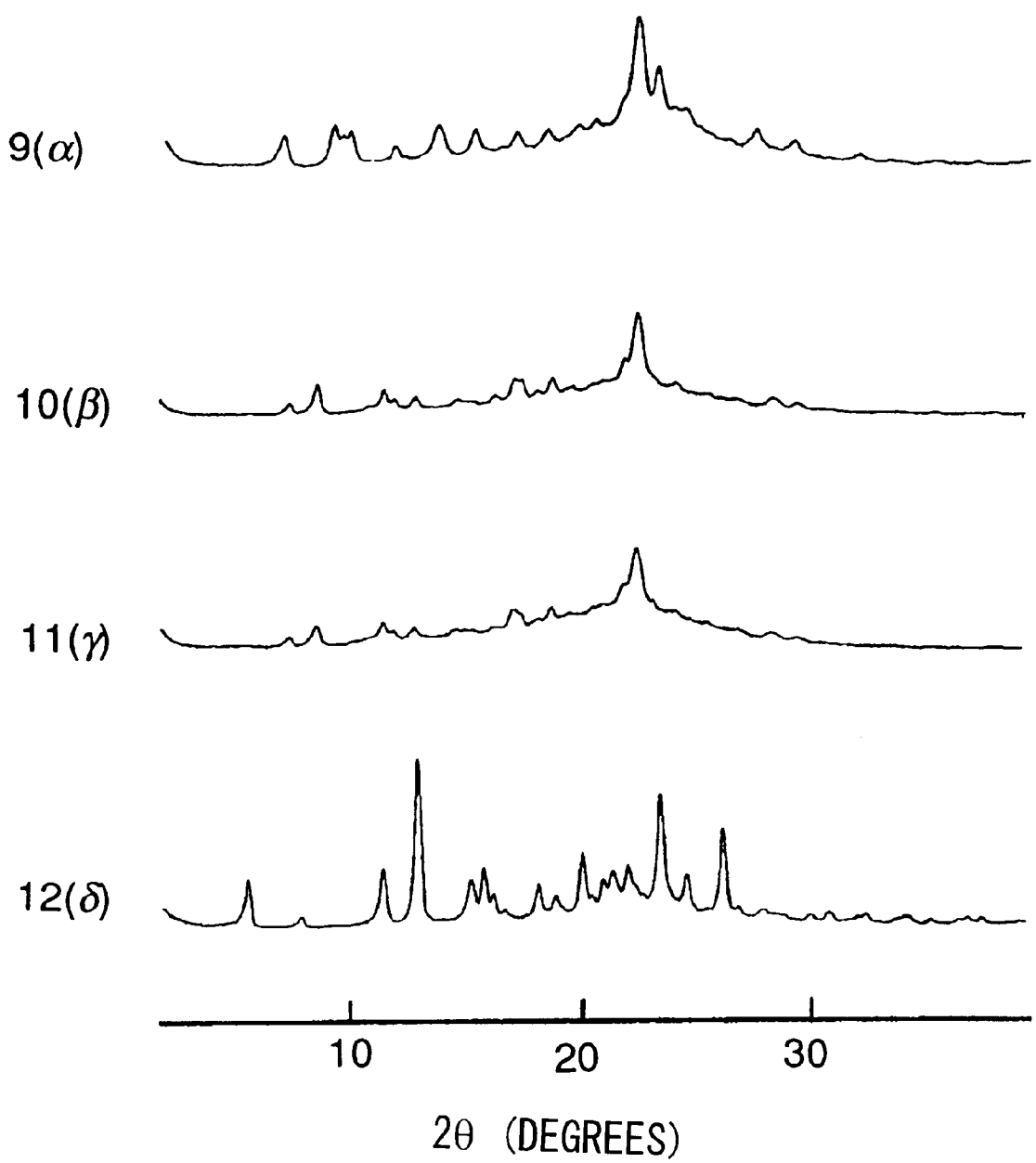
FIG. 3 is a schematic drawing pertaining to powder X-ray diffraction patterns for four types of crushed crystals of a quinolinone derivative. 9(α) is the powder X-ray diffraction pattern of the crushed α crystal form, 10(β) is that of the crushed β crystal form, 11(γ) is that of the crushed γ crystal form, and 12(δ) is that of the crushed δ crystal form.
Figure 4:
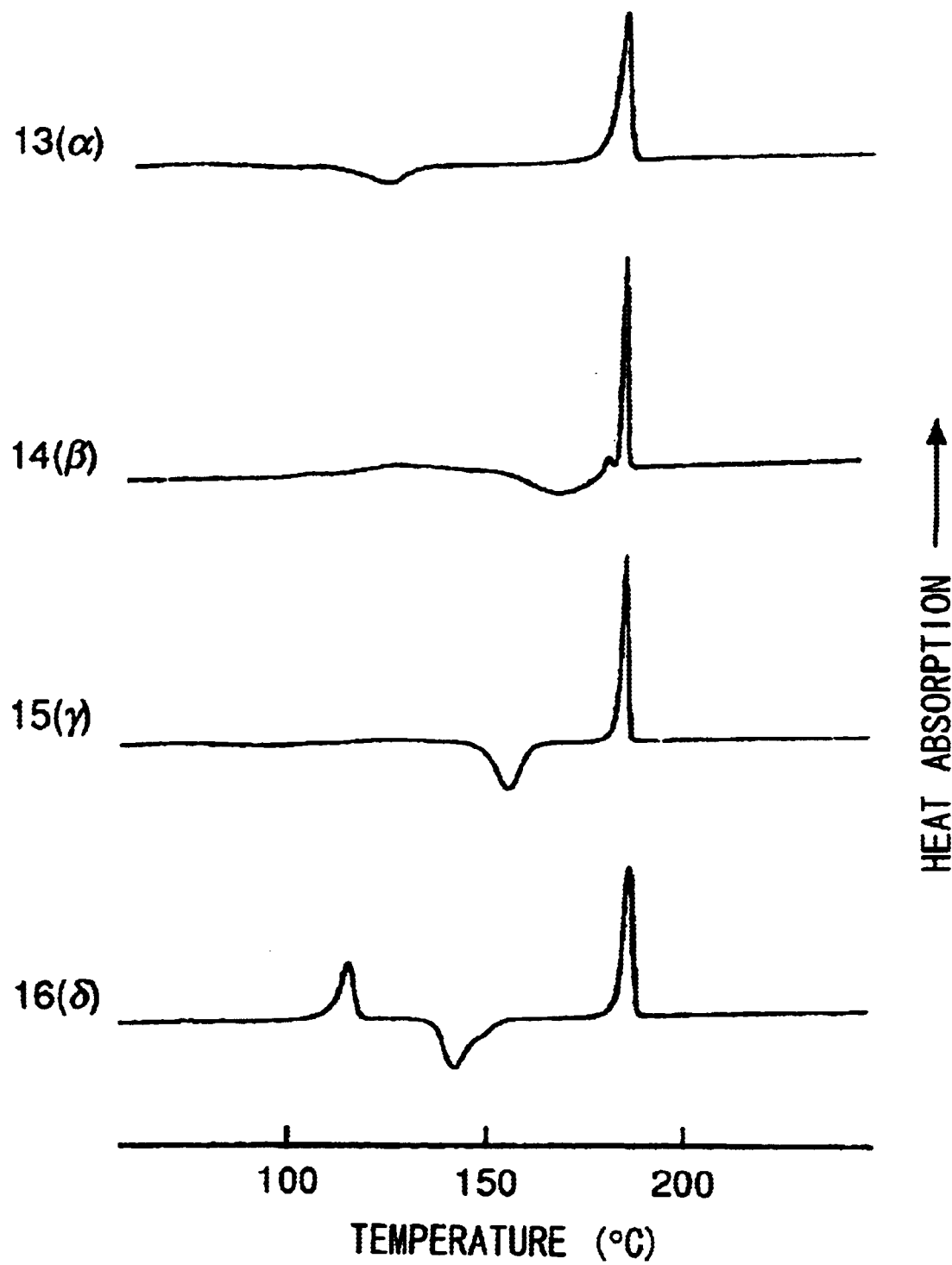
FIG. 4 is a schematic drawing pertaining to DSC curves for four types of crushed crystals of a quinolinone derivative. 13(α) is the DSC curve of the crushed α crystal form, 14(β) is that of the crushed δ crystal form, 15(γ) is that of the crushed γ crystal form, and 16(δ) is that of the crushed δ crystal form.

An example of the powder X-ray diffraction patterns measured under the same conditions of each crushed crystal obtained by crushing each of the crystal forms is shown in FIG. 3. Each crushed crystal exhibits a considerable decrease in the diffraction peak intensity as compared with the powder X-ray diffraction patterns of each crystal form prior to crushing. In addition, the DSC curves measured under the same conditions for each of the crushed crystals are shown in FIG. 4.

In the case of the crushed α crystal form, an exothermic peak accompanying crystallization of an amorphous portion and an endothermic peak of the α-form crystal are observed in the vicinity of 124° C. In addition, in the case of the crushed β crystal form, crushed γ crystal form and crushed δ crystal form, since the endothermic peak of each crystal form is extremely small, an exothermic peak assumed to represent crystal dislocation along with an endothermic peak at the same temperature as the α crystal form are observed. Thus, a remarkable decrease in crystallinity and conversion to the amorphous form are observed for each crystal form due to crushing of the crystals in all cases.

Next, crystal forms having excellent bioabsorption were determined by evaluating absorption into bodies of various crystal forms and their crushed products of the quinolinone derivative represented with chemical formula (I) according to the maximum plasma concentration (Cmax) and area under the plasma concentration vs. time curve (AUC) obtained from absorption experiments in rats. As a result, the β crystal form, γ crystal form and δ crystal form along with their crushed products were determined to exhibit higher values for Cmax and AUC and have superior absorption into the bodies as compared with the α crystal form and its crushed product.

Thus, from the viewpoint of absorption into the body, a formulation of the quinolinone derivative represented with chemical formula (I) is preferably produced using the β crystal form, γ crystal form, δ crystal form, their crushed products or their mixtures, and is not preferably produced using the α crystal form. In addition, although crushing the β form, γ form and δ-form crystals used here results in increased absorption into the body, these crystals are not required to be crushed.

Moreover, as is indicated in the examples, the stability of each crystal form of the quinolinone derivative of the present invention was evaluated by a six-month photostability test. As a result, the content of each crystal form gradually decreased over time, and each crystal form clearly tended to be unstable with respect to light. In particular, the δ crystal form was remarkably unstable as compared with the other crystal forms, while in contrast, the α crystal form, β crystal form and γ crystal form were clearly determined to have comparatively superior stability.

Thus, although the β crystal form, γ crystal form and δ crystal form are selected as preferable crystal forms from the viewpoint of superior bioabsorption, by additionally selecting from the viewpoint of stability, and particularly photostability, the use of the β crystal form and/or γ crystal form, having both superior bioabsorption and storage stability, is preferable as a quinolinone derivative formulation for the formulation of the quinolinone derivative represented with chemical formula (I). Furthermore, the β crystal form and/or γ crystal form used here may or may not be crushed.

The β crystal form and/or γ crystal form can be obtained as their respective crystal forms or as a mixture of both crystals by recrystallizing the quinolinone derivative represented with chemical formula (I) using ethanol as the recrystallization solvent in accordance with known routine recrystallization methods, followed by removing the ethanol by drying under reduced pressure. The β-form crystals are obtained following ethanol recrystallization by drying under reduced pressure at a comparatively low temperature, namely 0–60° C. and preferably 30–50° C.

In addition, the γ-form crystals are obtained following ethanol recrystallization by drying under reduced pressure at a comparatively high temperature, namely 60–110° C. and preferably 70–90° C. In the case of selectively obtaining each crystal form, drying under reduced pressure should be carried out by selecting a drying temperature suitable for each crystal form.

The β-form crystals and/or γ-form crystals of the quinolinone derivative represented with chemical formula (I) used in the present invention are not necessarily limited to being that obtained by recrystallization from ethanol, but rather β-form crystals and/or γ-form crystals obtained by other methods can also be used without problem.

For example, the γ-form crystals can also be obtained by a method in which, after dissolving the quinolinone derivative represented with chemical formula (I) in a mixed solvent of 5 parts methylene chloride and 1 part ethanol, hexane is added to precipitate the quinolinone derivative, and said crystals can also be used in the present invention without any particular problems.

A pharmaceutical formulation having for its active ingredient the β-form crystals and/or γ-form crystals of the quinolinone derivative represented with chemical formula (I) can be administered orally (taken internally or inhaled) or parenterally (e.g., intravenous administration, subcutaneous administration, transcutaneous administration or intrarectal administration), and can be prepared into a formulation form suitable for the respective administration method at the time of administration.

The formulation can be prepared in various formulation forms such as tablets, capsules, granules, grains, powders, troches, sublingual formulations, suppositories, ointments, injections, emulsions, suspensions, syrups, aerosols, and the like according to the specific application.

Particularly preferable formulation forms include capsules, coated granules, coated tablets and sugar-coated tablets, which can block lights. When preparing these formulations, said formulations can be formulated in accordance with known methods using non-toxic additives normally used in this type of formulation, examples of which include vehicles, binders, disintegration agents, lubricants, preservatives, antioxidants, isotonic agents, buffers, coating agents, correctives, dissolving assistants, bases, dispersants, stabilizers, colorants, and the like. Said formulations are preferably formulated in accordance with known methods using antioxidants and/or lubricants in particular.

The following lists specific examples of these non-toxic additives.

Examples of antioxidants include sulfites (sodium sulfite, sodium hydrogensulfite, etc.), rongalite, erysorbic acid, L-ascorbic acid, cysteine, thioglycerol, butylhydroxy anisole, dibutylhydroxy toluene, propyl gallate, ascorbic palmitate, dl-a-tocopherol, and the like, and a preferable example is L-ascorbic acid. The addition of said antioxidant enables oxidation of the quinolinone derivative to be inhibited. The amount of said agent added may be within a range at which the above effects are demonstrated, and is typically 0.01–100 wt %, and preferably 0.1–50 wt %, relative to the amount of quinolinone derivative.

Examples of lubricants include stearic acid, calcium stearate, magnesium stearate, talc, silicic acid and its salts (such as light silicic anhydride and naturally-occurring aluminum silicate), titanium oxide, calcium hydrogen phosphate, dry aluminum hydroxide gel, macrogall, sucrose fatty acid ester (e.g., RYOTO Sugar Ester P-1670, Mitsubishi Chemicals and Foods), and the like, and a preferable example is sucrose fatty acid ester. The addition of said lubricant prevents distortion of the crystal structure due to pressure, friction or heat during crushing or mixing of quinolinone derivative crystals, thereby making it possible to inhibit oxidative decomposition. The amount of said agent added may be within the range that allows the above effects to be demonstrated, and is typically 0.01–100 wt %, and preferably 0.1–50 wt %, relative to the amount of quinolinone derivative.

Examples of vehicles include starch and its derivatives (such as dextrin and carboxymethyl starch), cellulose and its derivatives (such as methyl cellulose and hydroxypropyl cellulose), sugars (such as lactose, refined sugar, and glucose), silicic acid and silicates (such as naturally-occurring aluminum silicate and magnesium silicate), carbonates (such as calcium carbonate, magnesium carbonate, and sodium bicarbonate), aluminum-magnesium hydroxide, synthetic hydrotalcite, polyoxyethylene derivatives, glycerin monostearate, sorbitan monooleate, sucrose fatty acid ester, and the like, and sucrose fatty acid ester is preferable.

Examples of binders include starch and its derivatives (such as alpha-converted starch and dextrin), cellulose and its derivatives (such as ethyl cellulose, sodium carboxymethyl cellulose, and hydroxypropylmethyl cellulose), gum arabic, tragacanth gum, gelatin, sugars (such as glucose and refined sugar), ethanol, polyvinyl alcohol, sucrose fatty acid ester, and the like, and sucrose fatty acid ester is preferable.

Examples of disintegration agents include starch and its derivatives (such as carboxymethyl starch and hydroxypropyl starch), cellulose and its derivatives (such as sodium carboxymethyl cellulose, crystal cellulose, and hydroxypropylmethyl cellulose), carbonates (such as calcium carbonate and calcium hydrogen carbonate), tragacanth gum, gelatin, agar, and sucrose fatty acid ester, and sucrose fatty acid ester is preferable.

Examples of preservatives include paraoxybenzoate esters, sulfites (such as sodium sulfite and sodium pyrosulfite), phosphates (such as sodium phosphate, calcium polyphosphate, sodium polyphosphate, and sodium metaphosphate), alcohols (such as chlorobutanol and benzyl alcohol), benzalkonium chloride, benzetonium chloride, phenol, cresol, chlorocresol, dehydroacetic acid, sodium dehydroacetate, glycerin sorbate, sugars, and the like.

Examples of isotonic agents include sodium chloride, sodium nitrate, potassium nitrate, dextrin, glycerin, glucose, and the like. In addition, examples of buffers include sodium carbonate, hydrochloric acid, boric acid, phosphates (such as sodium hydrogen phosphate), and the like.

Examples of coating agents include refined sugar, talc, gelatin, gum arabic, pluran, carnauba wax, cellulose derivatives (such as hydroxypropyl cellulose, cellulose acetophthalate, and hydroxypropyl methyl cellulose phthalate), shellac, polyvinyl pyrrolidone, polyvinyl pyridines (such as poly-2-vinylpyridine and poly-2-vinyl-5-ethylpyridine), polyvinylacetyldiethylaminoacetate, polyvinyl alcohol phthalate, methacrylate-methacrylic acid copolymer, sucrose fatty acid esters, and the like, and sucrose fatty acid ester is preferable.

Examples of colorants include edible tar pigments (such as edible red dye no. 2 and no. 3; yellow dye no. 4 and no. 5; and blue dye no. 1 and no. 2), iron oxide, titanium oxide, β-carotene, chlorophyll, lake pigments, and the like. Examples of correctives include sugars (such as glucose, refined sugar, and lactose), sodium saccharine, sugar-alcohols, and the like.

Examples of dissolving assistants include ethylenediamine, nicotinic amide, sodium saccharine, citric acid, citrates, sodium benzoate, soaps, polyvinylpyrrolidone, polysorbates, sorbitan fatty acid esters, glycerin, polypropylene glycol, benzyl alcohol, sucrose fatty acid ester, and the like, and sucrose fatty acid ester is preferable.

Examples of bases include fats (such as lard), vegetable oils (such as olive oil and sesame oil), animal oils, lanolinic acid, vaseline, paraffin, wax, resin, bentonite, glycerin, glycolic oil, higher alcohols (such as stearyl alcohol and cetanol), sucrose fatty acid ester, and the like, and sucrose fatty acid is preferable.

Examples of dispersants include gum arabic, tragacanth gum, cellulose derivatives (such as methyl cellulose), stearate polyesters, sorbitan sesquioleates, aluminum monostearate, sodium alginate, polysorbates, sorbitan fatty acid esters, sucrose fatty acid ester, and the like, and sucrose fatty acid ester is preferable.

In addition, a preferable example of a stabilizer is sucrose fatty acid ester.

Besides those described above, sucrose fatty acid esters are also used as surfactants, solubilizers, suspension agents, lubricants, antifoaming agents, emulsifiers, disintegration assistants, moisture-proofing agents and so forth. The amount of sucrose fatty acid ester added is 0.01–100 wt %, and preferably 0.1–50 wt %, relative to the amount of the quinolinone derivative.

In addition, although the content of the β-form crystal and/or γ-form crystal of the quinolinone derivative represented with chemical formula (I) in this formulation varies according to the formulation form, in general, it is preferably contained at a concentration of 0.01–100 wt %. Although the dose can be varied over a wide range according to the target species of warm-blooded animal including humans, the severity of the symptoms, the diagnosis of a physician, and so forth, in general, in the case of oral administration, the dose as the amount of active ingredient is 0.01–50 mg, and prefersbly 0.05–10 mg, per day per 1 kg of body weight, and in the case of parenteral administration, the dose as the amount of active ingredient is 0.01–10 mg, and preferably 0.05–5 mg, per day per 1 kg of body weight.

In addition, the above dose can be administered in a single administration or divided into several administrations, and can be suitably varied according to the severity of patient symptoms and diagnosis of a physician. Formulations having for their active ingredient the β-form crystal and/or γ-form crystal of the quinolinone derivative represented with chemical formula (I) of the present invention have superior absorption into bodies as well as superior stability, and are extremely useful as formulations of said quinolinone derivative, and particularly as formulations for the treatment of allergic diseases.

EXAMPLES

Although the following provides a more detailed explanation of the present invention through its examples and reference examples, the present invention is naturally not limited to the scope of these examples.
(Powder X-Ray Diffraction Measurement Method)
Powder X-ray diffraction patterns were measured in accordance with routine methods over a range of 2–60 using the Rigaku Denki RINT Ultima and a Cu—Kα beam under conditions of 40 kV and 30 mA.
(Differential Scanning Calorimetry (DSC) Method)
Differential scanning calorimetry was measured in accordance with routine methods over a range of 50–250° C. using the Perkin Elmer DSC7 under conditions of a temperature increase rate of 20° C. per minute.

Reference Example 1

α-form Crystals 80 ml of acetonitrile were added to 1.00 g of the quinolinone derivative represented with chemical formula (I) in a nitrogen atmosphere followed by stirring for 2 hours at 50° C. After cooling to 5° C. and stirring for 1 hour, the crystals were dried under reduced pressure at room temperature to obtain 966 mg of the α-form crystals. The results of measurement of the powder X-ray diffraction pattern are shown in 1(α) of FIG. 1, while the results of DSC analysis are shown in 5(α) of FIG. 2. The endothermic peak of DSC was observed at 187° C.

Reference Example 2

β-form Crystals 8 ml of ethanol were added to 1.00 g of the quinolinone derivative represented with chemical formula (I) in a nitrogen atmosphere and dissolved by refluxing while heating. After cooling to room temperature and stirring for 1 hour, the crystals were dried under reduced pressure at 30–50° C. to obtain 959 mg of the β-form crystals. The results of measurement of the powder X-ray diffraction pattern are shown in 2(β) of FIG. 1, while the results of DSC analysis are shown in 6(β) of FIG. 2. The endothermic peak of DSC was observed at 150° C.

Reference Example 3

γ-form Crystals 10 ml of methylene chloride and 2 ml of ethanol were added to 1.00 g of the quinolinone derivative represented with chemical formula (I) in a nitrogen atmosphere and dissolved. After adding 25 ml of hexane and stirring for 1 hour, the crystals were dried under reduced pressure at room temperature to obtain 953 mg of the γ-form crystals. The results of measurement of the powder X-ray diffraction pattern are shown in 3(γ) of FIG. 1, while the results of DSC analysis are shown in 7(γ) of FIG. 2. The endothermic peak of DSC was observed at 142° C.

Reference Example 4

δ-form Crystals 35 ml of acetone were added to 1.00 g of the quinolinone derivative represented with chemical formula (I) in a nitrogen atmosphere followed by stirring for 1 hour at 50° C. After cooling to 5° C. and stirring for 1 hour, the crystals were dried under reduced pressure at room temperature to obtain 909 mg of the δ-form crystals. The results of measurement of the powder X-ray diffraction pattern are shown in 4(δ) of FIG. 1, while the results of DSC analysis are shown in 8(δ) of FIG. 2. The endothermic peak of DSC was observed at 117° C.

Reference Example 5

γ-form Crystals 8 ml of ethanol were added to 1.00 g of the quinolinone derivative represented with chemical formula (I) in a nitrogen atmosphere and dissolved by refluxing while heating. After cooling to room temperature followed by stirring for 1 hour, the crystals were dried under reduced pressure at 70–90° C. to obtain 961 mg of the γ-form crystals. The results of measurement of the powder X-ray diffraction pattern and DSC analysis were the same as those of the γ-form crystals obtained in Reference Example 3.

Reference Example 6

Crushed Product of Each Crystal Form

Each of the above crystal forms was crushed for 10 minutes using an automated agate mortar, and examples of the powder X-ray diffraction patterns obtained by measuring each of the resulting crushed products using a Cu—Kα beam under conditions of 40 kV and 3 mA over a range of 2–60° in the same manner as previously described are shown in FIG. 3. In FIG. 3, the horizontal axis represents the angle, 2θ (degrees), while the vertical axis represents intensity (cps).

9(α) in FIG. 3 indicates the powder X-ray diffraction pattern of crushed α-form crystals, 10(β) indicates that of the crushed β-form crystals, 11(γ) indicates that of the crushed γ-form crystals, and 12(δ) indicates that of the crushed δ-form crystals. The crushed products of each crystal exhibited a remarkable decrease in diffraction peak intensity as compared with the powder X-ray diffraction patterns of each crystal form prior to crushing due to the decrease in the degree of crystallinity.

In addition, the DSC curves of the crushed products of each crystal form as measured under conditions of a temperature increase rate of 20° C./min over a measuring range of 50–250° C. as previously described are shown in FIG. 4. In FIG. 4, the horizontal axis represents temperature (°C.), while the vertical axis represents heat absorption (mW). 13(α) in FIG. 4 indicates the DSC curve of the crushed α-form crystals, 14(β) indicates that of the crushed β-crystals, 15(γ) indicates that of the crushed γ-form crystals, and 16(δ) indicates that of the crushed δ-form crystals.

In the case of the crushed α-form crystals, an exothermic peak accompanying crystallization of the amorphous portion and an endothermic peak of the α-form crystals were observed in the vicinity of 124° C. In addition, in the case of the crushed β-form, γ-form and δ-form crystals, since the endothermic peaks of each crystal form were extremely small, exothermic peaks assumed to represent crystal dislocation were observed in the vicinities of 170° C., 157° C. and 144° C., respectively, while endothermic peaks were observed at the same temperature as the α-form crystals. Thus, the degree of crystallinity was observed to decrease considerably due to crushing for all crystal forms, and conversion to an amorphous state was observed to occur in each crystal form.

Example 1
Absorption Test in Rats

A comparison of absorption into bodies of rats was conducted for each of the crystal forms and their crushed products of the quinolinone derivative represented with chemical formula (I). Furthermore, each of the crystal forms of the quinolinone derivative represented with chemical formula (I) were crushed using an automated agate mortar.

The following provides an explanation of the test method.

100 mg/kg of each sample were administered orally in a single administration using a gastric tube to 3 male SD rats (age 6 weeks) fasted for 16 hours. The samples were administered after suspending in 0.5% aqueous methyl cellulose solution and preparing to a concentration of 100 mg/5 ml. Following administration, blood samples were collected over time from the tail vein using heparin-treated glass tubes, and the quinolinone derivative concentrations of the resulting plasma were assayed by HPLC.

The maximum plasma concentration (Cmax) and area under the plasma concentration vs. time curve (AUC) were determined from the assayed values of the quinolinone derivative at each blood sampling time. Those results are shown in Table 1.

Furthermore, Cmax was determined using measured values, while AUC was determined by calculating according to a trapezoidal equation until the time of measurement, and using the elimination rate constant after that time. The Cmax and AUC of each crystal form of the quinolinone derivative represented with chemical formula (I) are described as comparative examples.

TABLE 1

| Sample | Cmax (μg/ml) | AUC (μg h/ml) |
|---|---|---|
| Crushed α-form crystals | 33 | 253 |
| Crushed β-form crystals | 67 | 586 |
| Crushed γ-form crystals | 65 | 575 |
| Crushed δ-form crystals | 63 | 597 |
| α-form crystals | 10 | 73 |
| β-form crystals | 41 | 375 |
| γ-form crystals | 38 | 325 |
| δ-form crystals | 51 | 512 |

As shown in Table 1, the β-form crystals, γ-form crystals, δ-form crystals and their crushed products were determined to exhibit higher Cmax and AUC values and demonstrate superior absorption as compared with the α-form crystals and its crushed product. In addition, regardless of whether crushed or not, the β-form crystals, γ-form crystals and δ-form crystals demonstrated superior absorption as compared with the α-form crystals.

Example 2
Photostability Test 0.5 g of each of the crystal forms of the quinolinone derivative represented with chemical formula (I) were filled into a transparent and sealed container in a nitrogen atmosphere, and were stored for 6 months under direct sunlight at room temperature.

The content of each crystal form of the quinolinone derivative represented with chemical formula (I) was assayed over time by HPLC followed by a comparison of stability. The results indicated as the residual rate based on a rate of 100% prior to storage are shown in Table 2.

TABLE 2

| | Residual rate of quinolinone derivative (%) | | | |
|---|---|---|---|---|
| Storage period | α-form crystals | β-form crystals | γ-form crystals | δ-form crystals |
| 0 days | 100 | 100 | 100 | 100 |
| 15 days | 99.1 | 98.7 | 98.9 | 96.2 |
| 1 month | 97.2 | 96.8 | 96.5 | 91.4 |
| 6 months | 85.1 | 84.5 | 84.1 | 57.3 |

As is shown in Table 2, the contents of each crystal form decreased over time, and each crystal exhibited the tendency of being unstable with respect to light. In particular, the residual rate after 6 months of the δ-form crystals was only 57.3%, and these crystals were determined to be extremely unstable as compared with the other crystal forms. In addition, the α-form crystals, β-form crystals and γ-form crystals were clearly relatively stable as compared with the δ-form crystals.

Example 3
Coated Granules

An example of a production method for coated granules is indicated below.
(Granule Formula)

TABLE 3

| Quinolinone derivative (β-form crystals) | 3.00 g |
|---|---|
| Lactose | 20.00 g |
| Starch | 6.70 g |
| Gelatin | 0.30 g |
| | 30.00 g |

(Coating Liquid Composition)

TABLE 4

| Hydroxypropyl cellulose | 40 mg |
|---|---|
| Glycerin fatty acid ester | 10 mg |
| Titanium oxide | 4 mg |
| Talc | 5 mg |
| Lake pigment | 1 mg |
| Purified water | 940 mg |
| Total | 1000 mg |

β-form crystals of the quinolinone derivative represented with chemical formula (I) were mixed with an equal amount of starch and crushed in a mortar. This was followed by the addition of lactose and the remaining starch and mixing. Separate from this, 300 mg of gelatin were added to 10 ml of purified water and dissolved while heating. After cooling, 10 ml of ethanol were added while stirring to prepare the gelatin liquid. This gelatin liquid was then added to and kneaded with the above mixture, and after granulating, the resulting granules were dried and graded to prepare granules. These granules were then coated in accordance with routine methods using 15 g of the above coating liquid to produce coated granules.

Example 4

Coated Tablets

An example of a production method for coated tablets is indicated below.

(Uncoated Tablet Formula)

TABLE 5

| | |
|---|---|
| Quinolinone derivative (β-form crystals) | 5 mg |
| Lactose | 62 mg |
| Starch | 30 mg |
| Talc | 2 mg |
| Magnesium stearate | 1 mg |
| | 100 mg/tablet |

(Coating Liquid Composition)

TABLE 6

| | |
|---|---|
| Hydroxypropyl cellulose | 40 mg |
| Glycerin fatty acid ester | 10 mg |
| Titanium oxide | 4 mg |
| Lake pigment | 1 mg |
| Ethanol | 945 mg |
| Total | 1000 mg |

Coated tablets were produced using 30 times the amount of the above formulation. Namely, 150 mg of γ-form crystals of the quinolinone derivative represented with chemical formula (I) were crushed in a mortar followed by the addition of lactose and starch and mixing. 10% starch paste was then added to the above mixture followed by kneading and granulation. After drying, talc and magnesium stearate were mixed in followed by forming into tablets in accordance with routine methods to obtain uncoated tablets. These uncoated tablets were then coated in accordance with routine methods using 1.8 g of the above coating liquid to produce coated tablets.

Example 5

Coated Tablets

An example of a production method for coated tablets is indicated below.

(Uncoated Tablet Formula)

TABLE 7

| | |
|---|---|
| Quinolinone derivative (β-form crystals) | 5 mg |
| Lactose | 61 mg |
| Starch | 30 mg |
| Talc | 2 mg |
| L-ascorbic acid | 1 mg |
| Magnesium stearate | 1 mg |
| | 100 mg/tablet |

(Coating Liquid Composition)

TABLE 8

| | |
|---|---|
| Hydroxypropyl cellulose | 40 mg |
| Glycerin fatty acid ester | 10 mg |
| Titanium oxide | 4 mg |
| Lake pigment | 1 mg |
| Ethanol | 945 mg |
| Total | 1000 mg |

Coated tablets were produced using 30 times the amount of the above formulation. Namely, L-ascorbic acid was added to 150 mg of γ-form crystals of the quinolinone derivative represented with chemical formula (I) followed by crushing in a mortar and mixing. Lactose and starch were then added and mixed. Moreover, 10% starch paste was then added to the above mixture followed by kneading and granulation. After drying, talc and magnesium stearate were mixed in followed by forming into tablets in accordance with routine methods to obtain uncoated tablets. These uncoated tablets were then coated in accordance with routine methods using 1.8 g of the above coating liquid to produce coated tablets.

Example 6

Coated Tablets

An example of a production method for coated tablets is indicated below.

(Uncoated Tablet Formula)

TABLE 9

| | |
|---|---|
| Quinolinone derivative (β-form crystals) | 20 mg |
| 6% hydroxypropyl cellulose lactose | 75 mg |
| Talc stearate | 2 mg |
| Potato starch | 3 mg |
| | 100 mg/tablet |

(Coating Liquid Composition)

TABLE 10

| | |
|---|---|
| Hydroxypropyl cellulose | 40 mg |
| Glycerin fatty acid ester | 10 mg |
| Titanium oxide | 4 mg |
| Talc | 5 mg |
| Lake pigment | 1 mg |
| Purified water | 940 mg |
| Total | 1000 mg |

Coated tablets were produced using 30 times the amount of the above formulation. Namely, 6 g of hydroxypropyl cellulose were dissolved in a suitable amount of ethanol followed by the addition of 94 g of lactose and kneading. After allowing to dry somewhat, the mixture was graded with a no. 60 sieve to obtain 6% hydroxypropyl cellulose lactose. In addition, magnesium stearate and talc were mixed at a ratio of 1:4 to obtain talc stearate.

The γ-form crystals of the quinolinone derivative represented with chemical formula (I), 6% hydroxypropyl cellulose lactose, talc stearate, and potato starch were mixed well and formed into tablets in accordance with routine methods to obtain uncoated tablets. These uncoated tablets were then coated in accordance with routine methods using 1.5 g of the above coating liquid to produce coated tablets.

Example 7

Coated Tablets

An example of a production method for coated tablets is indicated below.

(Uncoated Tablet Formula)

TABLE 11

| | |
|---|---|
| Quinolinone derivative (β-form crystals) | 20 mg |
| 6% hydroxypropyl cellulose lactose | 73 mg |
| Sucrose fatty acid ester | 2 mg |
| Talc stearate | 2 mg |
| Potato starch | 3 mg |
| | 100 mg/tablet |

(Coating Liquid Composition)

TABLE 12

| | |
|---|---|
| Hydroxypropyl cellulose | 40 mg |
| Glycerin fatty acid ester | 10 mg |
| Titanium oxide | 4 mg |
| Talc | 5 mg |
| Lake pigment | 1 mg |
| Purified water | 940 mg |
| Total | 1000 mg |

Coated tablets were produced using 30 times the amount of the above formulation. Namely, 6 g of hydroxypropyl cellulose were dissolved in a suitable amount of ethanol followed by the addition of 94 g of lactose and kneading. After allowing to dry somewhat, the mixture was graded with a no. 60 sieve to obtain 6% hydroxypropyl cellulose lactose. In addition, magnesium stearate and talc were mixed at a ratio of 1:4 to obtain talc stearate.

After adding sucrose fatty acid ester to the γ-form crystals of the quinolinone derivative represented with chemical formula (I) and mixing well, 6% hydroxypropyl cellulose lactose, talc stearate, and potato starch were added and mixed well followed by forming into tablets in accordance with routine methods to obtain uncoated tablets. These uncoated tablets were then coated in accordance with routine methods using 1.5 g of the above coating liquid to produce coated tablets.

Example 8

Sugar-Coated Tablets

An example of production of sugar-coated tablets is indicated below.

(Uncoated Tablet Formula)

TABLE 13

| | |
|---|---|
| Quinolinone derivative (β-form crystals) | 60 mg |
| Lactose | 93 mg |
| Cornstarch | 38 mg |
| Hydroxypropyl cellulose | 6 mg |
| Talc | 2 mg |
| Magnesium stearate | 1 mg |
| | 200 mg/tablet |

(Sub-Coating Liquid Composition)

TABLE 14

| | |
|---|---|
| Refined sugar | 850 mg |
| Powdered gum arabic | 50 mg |
| Purified water | 450 mg |
| | 1350 mg |

(Smoothing Liquid Composition)

TABLE 15

| | |
|---|---|
| Refined sugar | 850 mg |
| Gelatin | 5 mg |
| Powdered gum arabic | 20 mg |
| Purified water | 450 mg |
| Precipitated calcium carbonate | 1000 mg |
| Dye liquid | 5 mg |
| Total | 2330 mg |

(Coloring Liquid Composition)

TABLE 16

| | |
|---|---|
| Refined sugar | 850 mg |
| Gelatin | 5 mg |
| Purified water | 450 mg |
| Dye liquid | 3 mg |
| Total | 1308 mg |

(Finishing Liquid Composition)

TABLE 17

| | |
|---|---|
| Refined sugar | 850 mg |
| Purified water | 450 mg |
| Dye liquid | 3 mg |
| Total | 1303 mg |

(Dye Liquid Composition)

TABLE 18

| | |
|---|---|
| Red dye no. 3 | 30 mg |
| Purified water | 270 mg |
| Total | 300 mg |

Coated tablets were produced using 300 times the amount of each of the above formulations. Namely, 18 g of β-form crystals of the quinolinone derivative represented with chemical formula (I) were filled into a mortar and crushed followed by mixing well while adding lactose and cornstarch. A suitable amount of purified water was then added to hydroxypropyl cellulose followed by addition to the above mixture, kneading and granulation.

After drying, talc and magnesium stearate were mixed and formed into tablets in accordance with routine methods to obtain uncoated tablets. The uncoated tablets then underwent steps consisting of sub-coating, smoothing, coloring, finishing, and polishing in accordance with routine methods using 1.00 g of the above sub-coating liquid, 1.73 g of the smoothing liquid, 0.97 g of the coloring liquid, and 0.97 g of the finishing liquid to produce sugar-coated tablets.

Example 9

10 mg Capsules

An example of production of capsules is indicated below.

TABLE 19

| | |
|---|---|
| Quinolinone derivative (β-form crystals) | 300 mg |
| Lactose | 2000 mg |
| Starch | 670 mg |
| Gelatin | 30 mg |
| Total | 3000 mg |

Granules were produced using the same method as Example 3 after which 100 mg aliquots of said granules were filled into light-blocking capsules to produce capsules.

Example 10

20 mg Capsules

An example of production of capsules is indicated below.

TABLE 20

| | |
|---|---|
| Quinolinone derivative | 600 mg |
| Lactose | 1500 mg |
| Starch | 651 mg |
| Sucrose fatty acid ester | 150 mg |
| Crystal cellulose | 60 mg |
| Hydroxypropyl cellulose | 39 mg |
| Total | 3000 mg |

Sucrose fatty acid ester was added and mixed well with the β-form crystals of the quinolinone derivative represented with chemical formula (I) in a mortar. Lactose, starch, and crystal cellulose were added to this mixture and mixed well. Separate from this, a suitable amount of purified water was added to hydroxypropyl cellulose, after which it was added to the above mixture followed by kneading and granulation. After drying, the granules were graded to prepare a granular formulation. 100 mg aliquots of said granules were filled into light-blocking capsules to produce capsules.

Example 11

50 mg Capsules

An example of production of capsules is indicated below.

TABLE 21

| | |
|---|---|
| Quinolinone derivative | 1500 mg |
| Lactose | 1025 mg |
| Starch | 376 mg |
| Crystal cellulose | 60 mg |
| Hydroxypropyl cellulose | 39 mg |
| Total | 3000 mg |

Lactose, starch and crystal cellulose were added to the β-form crystals of the quinolinone derivative represented with chemical formula (I) in a mortar while mixing well. Separate from this, a suitable amount of purified water was added to hydroxypropyl cellulose, after which it was added to the above mixture followed by kneading and granulation. After drying, the granules were graded to prepare a granular formulation. 100 mg aliquots of said granules were filled into light-blocking capsules to produce capsules.

Example 12

50 mg Capsules

An example of production of capsules is indicated below.

TABLE 22

| | |
|---|---|
| Quinolinone derivative | 1500 mg |
| Lactose | 875 mg |
| Starch | 376 mg |
| L-ascorbic acid | 150 mg |
| Crystal cellulose | 60 mg |
| Hydroxypropyl cellulose | 39 mg |
| Total | 3000 mg |

L-ascorbic acid was added and mixed well with the β-form crystals of the quinolinone derivative represented with chemical formula (I) in a mortar. Lactose, starch and crystal cellulose were added to this mixture and mixed well. Separate from this, a suitable amount of purified water was added to hydroxypropyl cellulose, after which it was added to the above mixture followed by kneading and granulation. After drying, the granules were graded to prepare a granular formulation. 100 mg aliquots of said granules were filled into light-blocking capsules to produce capsules.

Example 13

50 mg Capsules

An example of production of capsules is indicated below.

TABLE 23

| | |
|---|---|
| Quinolinone derivative | 1500 mg |
| Lactose | 875 mg |
| Starch | 376 mg |
| Sucrose fatty acid ester | 150 mg |
| Crystal cellulose | 60 mg |
| Hydroxypropyl cellulose | 39 mg |
| Total | 3000 mg |

Sucrose fatty acid ester was added and mixed well with the β-form crystals of the quinolinone derivative represented with chemical formula (I) in a mortar. Lactose, starch, and crystal cellulose were added to this mixture and mixed well. Separate from this, a suitable amount of purified water was added to hydroxypropyl cellulose, after which it was added to the above mixture followed by kneading and granulation. After drying, the granules were graded to prepare a granular formulation. 100 mg aliquots of said granules were filled into light-blocking capsules to produce capsules.

Example 14

50 mg Capsules

An example of production of capsules is indicated below.

TABLE 24

| | |
|---|---|
| Quinolinone derivative | 1500 mg |
| Lactose | 875 mg |
| Starch | 376 mg |
| Sucrose fatty acid ester | 75 mg |
| L-ascorbic acid | 75 mg |
| Crystal cellulose | 60 mg |
| Hydroxypropyl cellulose | 39 mg |
| Total | 3000 mg |

L-ascorbic acid and sucrose fatty acid ester were added and mixed well with the β-form crystals of the quinolinone derivative represented with chemical formula (I) in a mortar. Lactose, starch, and crystal cellulose were added to this mixture while mixing well. Separate from this, a suitable amount of purified water was added to hydroxypropyl cellulose, after which it was added to the above mixture followed by kneading and granulation. After drying, the granules were graded to prepare a granular formulation. 100 mg aliquots of said granules were filled into light-blocking capsules to produce capsules.

Example 15

Formulation Stability Test

Stability tests were performed using the granules produced in Examples 11, 12 and 13.

0.5 g aliquots of the granules produced in Examples 11, 12 and 13 were filled into brown, sealed containers and stored for 2 weeks at 80° C. and relative humidity of 50%. The content of the quinolinone derivative represented with chemical formula (I) was assayed by HPLC to compare stability. The results indicating as the residual rate based on a rate of 100% prior to storage are shown in Table 25.

TABLE 25

| | Residual rate of quinolinone derivative (%) | | |
|---|---|---|---|
| Storage period | Example 11 | Example 12 (5% ascorbic acid) | Example 13 (5% sucrose fatty acid ester) |
| Day 0 | 100 | 100 | 100 |
| Day 14 | 89.3 | 100 | 97.4 |

As shown in Table 25, in contrast to the residual rate after 14 days being only 89.3% for the formulation not containing ascorbic acid or sucrose fatty acid ester, the residual rates of the formulations containing ascorbic acid and sucrose fatty acid ester were 100% and 97.4%, respectively. Accordingly, stability was improved as a result of containing ascorbic acid and sucrose fatty acid ester.

INDUSTRIAL APPLICATION

The present invention provides a quinolinone derivative formulation, and its production method, having for its active ingredient the β crystal form and/or γ crystal form of the quinolinone derivative represented with chemical formula (I), which is useful as a pharmaceutical, and particularly as an antiallergic, which has superior bioabsorption and stability.

What is claimed is:

1. A quinolinone derivative formulation having for its active ingredient a β crystal form and/or a γ crystal form of a quinolinone derivative represented with chemical formula (I):

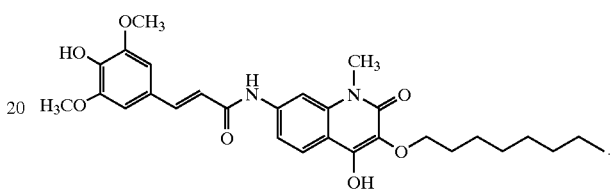

2. A quinolinone derivative formulation according to claim 1, further comprising an antioxidant and/or a lubricant.

3. A quinolinone derivative formulation according to claim 1, wherein the β crystal form and/or the γ crystal form is obtained by recrystallizing from ethanol.

4. A quinolinone derivative formulation according to claim 1, wherein the formulation is a formulation form selected from capsules; coated granules, coated tablets, or sugar-coated tablets, which can block lights.

* * * * *